(12) United States Patent
Haveri

(10) Patent No.: US 6,769,626 B1
(45) Date of Patent: Aug. 3, 2004

(54) DEVICE AND METHOD FOR DETECTING AND CONTROLLING LIQUID SUPPLY TO AN APPARATUS DISCHARGING LIQUIDS

(75) Inventor: Heikki Haveri, Helsinki (FI)

(73) Assignee: Instrumentarium Corp., Helsinki (FI)

( * ) Notice: Subject to any disclaimer, the term of this patent is extended or adjusted under 35 U.S.C. 154(b) by 45 days.

(21) Appl. No.: 09/699,049

(22) Filed: Oct. 30, 2000

(51) Int. Cl.$^7$ ................................................. B05B 3/04
(52) U.S. Cl. ................................. 239/102.2; 239/102.1; 239/337; 239/338; 128/200.12; 128/200.16
(58) Field of Search ........................... 239/102.1, 102.2, 239/337, 338, 590.5; 128/200.16, 200.12, 200.14, 200.18

(56) References Cited

U.S. PATENT DOCUMENTS

| | | | |
|---|---|---|---|
| 3,164,990 A | * | 1/1965 | Henness et al. ......... 73/861.71 |
| 3,812,854 A | | 5/1974 | Michaels et al. |
| 4,283,945 A | | 8/1981 | Knoll |
| 5,152,456 A | | 10/1992 | Ross et al. |
| 5,261,601 A | | 11/1993 | Ross et al. |
| 5,299,739 A | | 4/1994 | Takahaski et al. |
| 5,443,059 A | | 8/1995 | Koch et al. |
| 5,487,378 A | | 1/1996 | Robertson et al. |
| 5,518,179 A | | 5/1996 | Humberstone et al. |
| 5,586,550 A | | 12/1996 | Ivri et al. |
| 5,716,001 A | * | 2/1998 | Wakeman et al. ....... 239/590.5 |
| 5,758,637 A | | 6/1998 | Ivri et al. |
| 5,938,117 A | | 8/1999 | Ivri |
| 5,996,903 A | * | 12/1999 | Asai et al. ............... 239/102.2 |
| 6,048,328 A | | 4/2000 | Haller et al. |
| 6,076,519 A | | 6/2000 | Johnson |
| 6,085,740 A | | 7/2000 | Ivri et al. |
| 6,158,431 A | | 12/2000 | Poole |
| 6,192,882 B1 | | 2/2001 | Gonda |
| 6,196,219 B1 | * | 3/2001 | Hess et al. ............... 239/102.2 |

FOREIGN PATENT DOCUMENTS

| | | |
|---|---|---|
| DE | 37 10 141 | 10/1988 |
| FR | 798007 | 10/1997 |
| GB | 2099710 | 12/1982 |
| GB | 2272389 | 5/1994 |
| WO | 92/11050 | 7/1992 |

\* cited by examiner

Primary Examiner—Robin O. Evans
(74) Attorney, Agent, or Firm—Andrus, Sceales, Starke & Sawall, LLP

(57) ABSTRACT

An improved device and method for measuring the amount of liquid to be discharged that is present in an apparatus, such as a nebulizer. A first member has holes through which the liquid passes to be nebulized. A second member is spaced from the first member so that a volume is defined in the nebulizer by the area of mutual overlap of the first and second members and the amount of spacing between them. The first and second members are formed to establish a mutual capacitance that reflects the amount of liquid in the volume. A measuring circuit measures the capacitance existing between the first and second members and hence the amount of liquid in the nebulizer. The capacitance measurement can be used to control the supply of liquid into the volume in the nebulizer.

29 Claims, 5 Drawing Sheets

Figure 1:
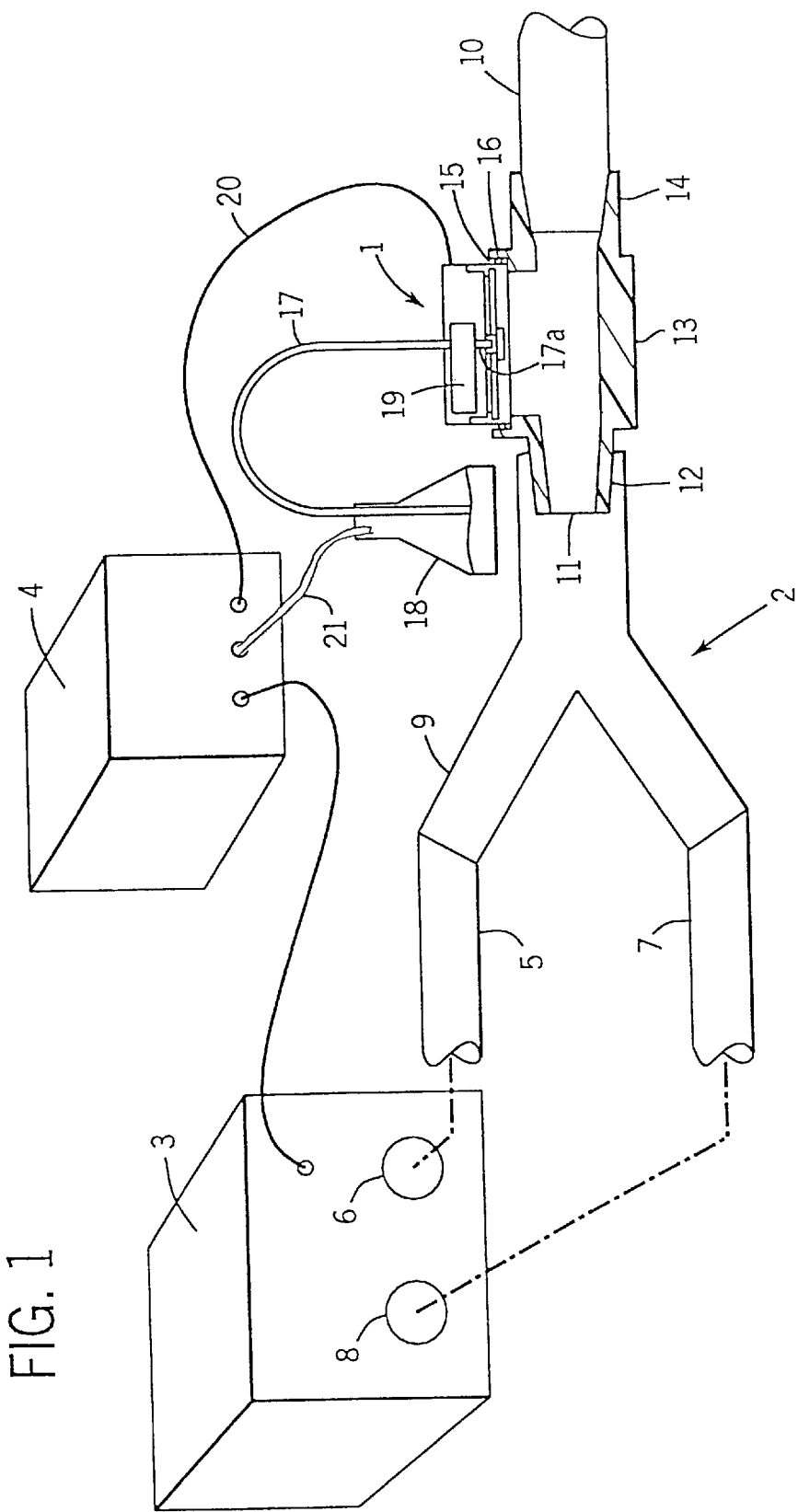
Figure 2A:
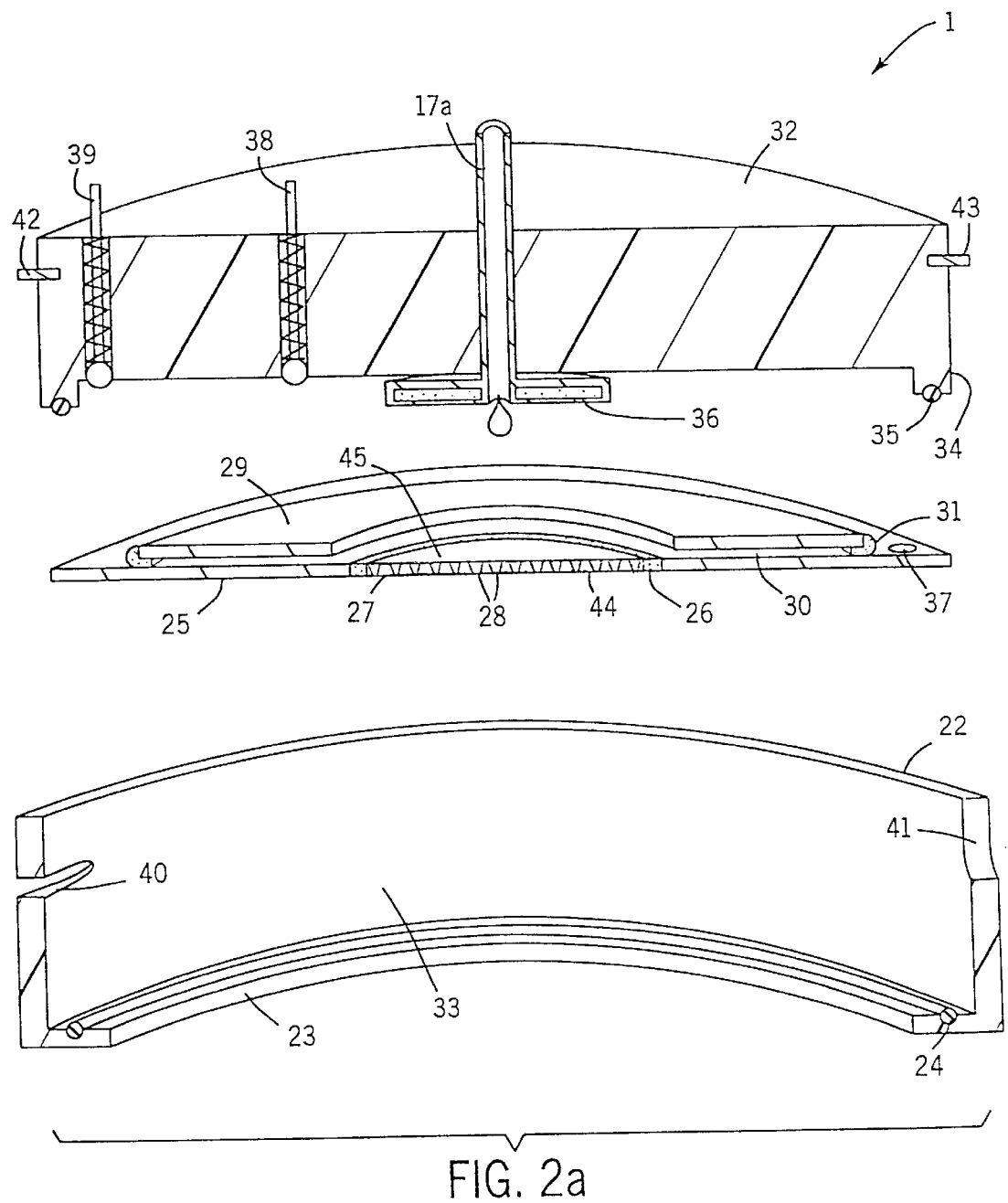
Figure 3:
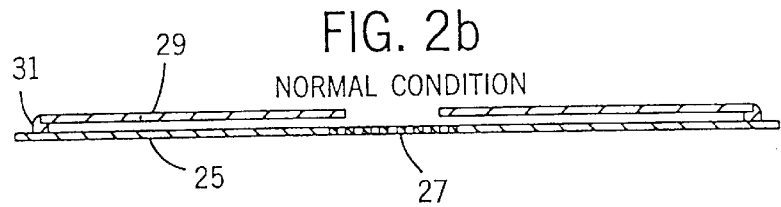
Figure 3:
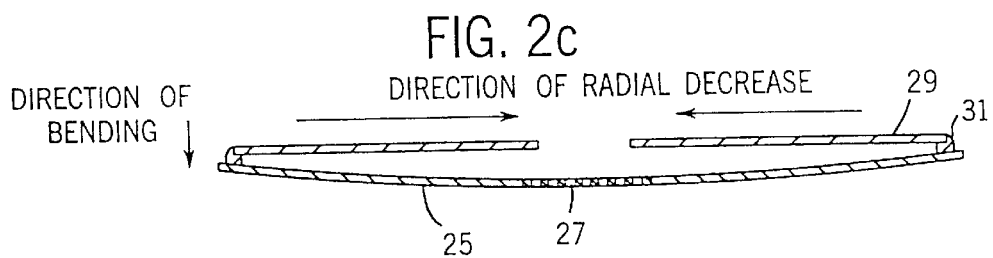
Figure 3:
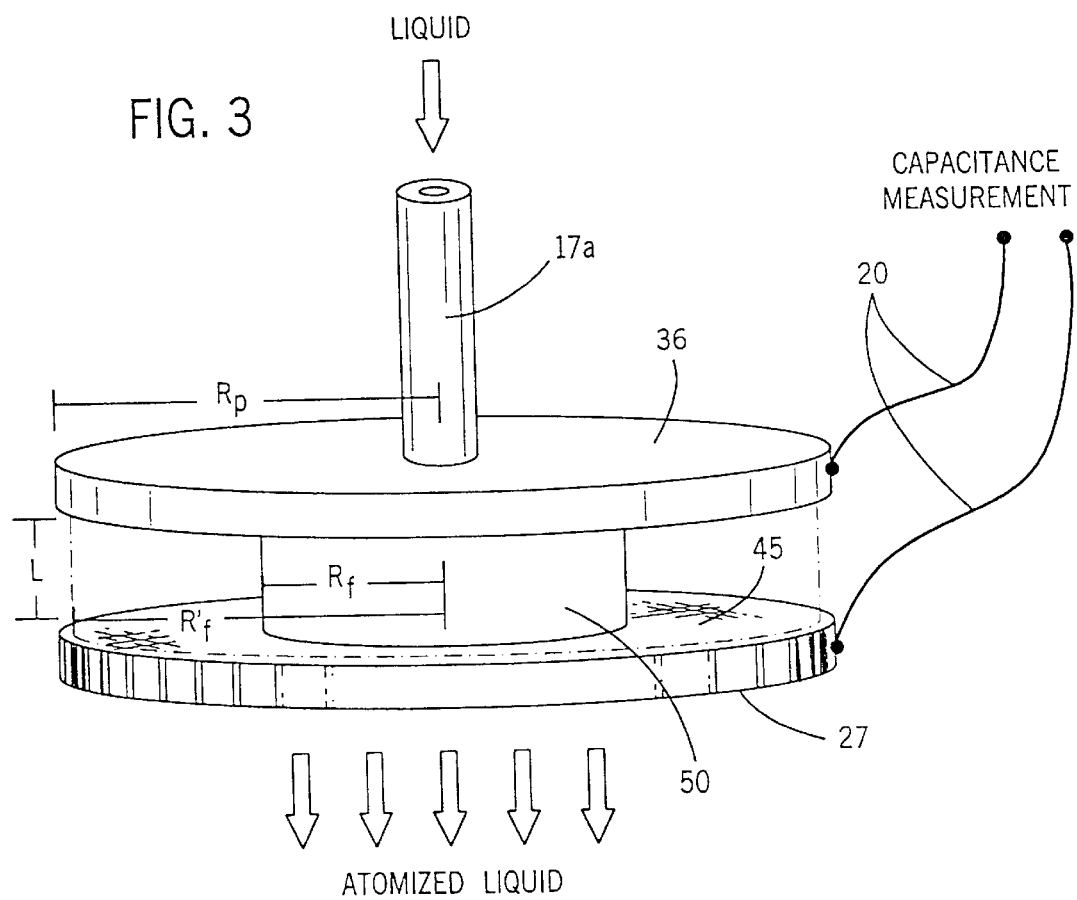
Figure 4:
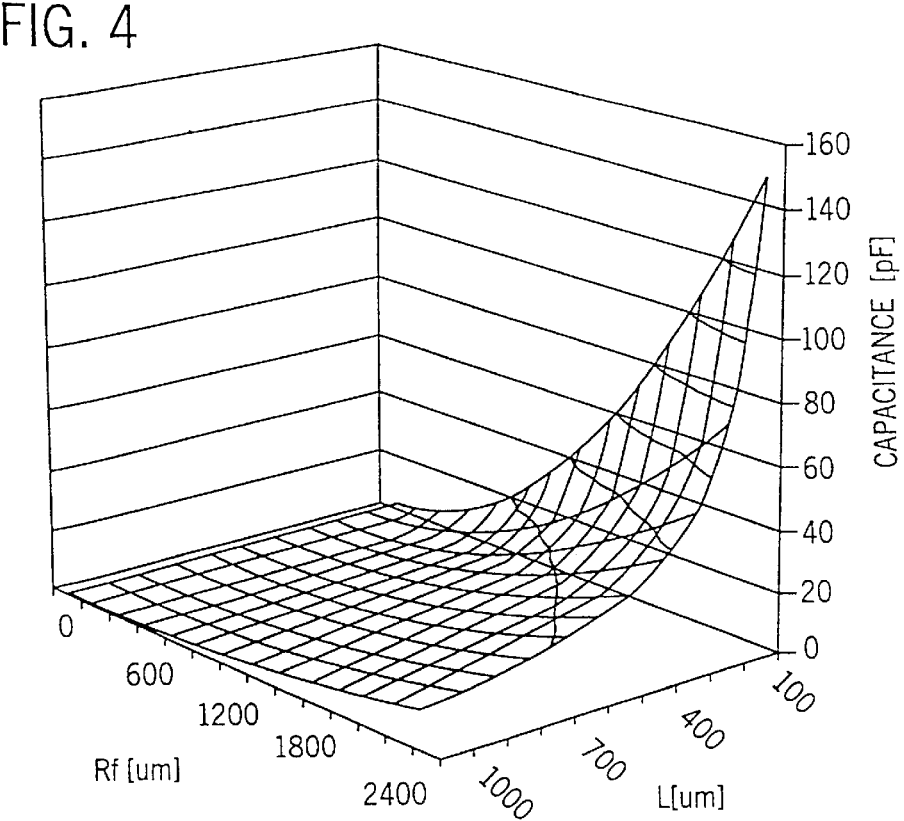
Figure 5:
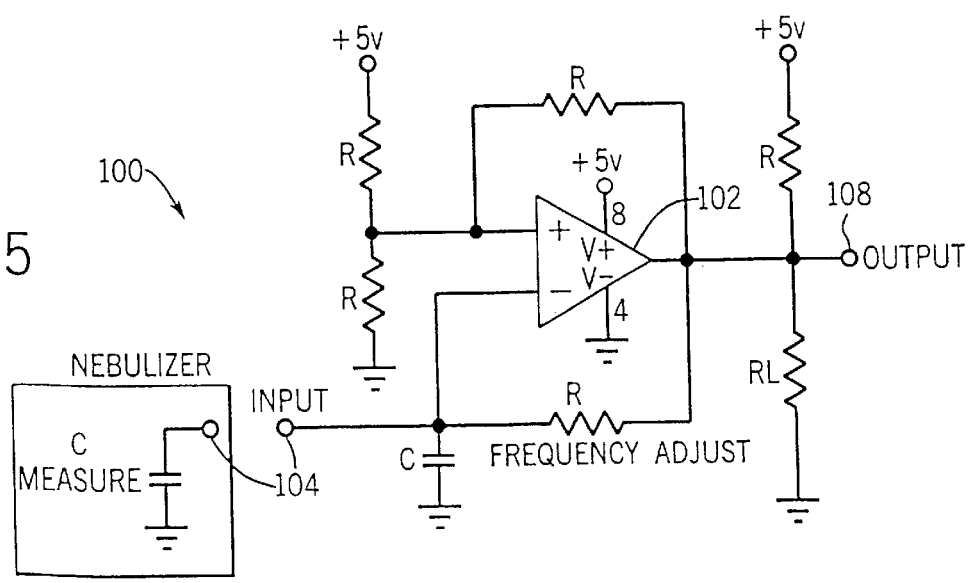
Figure 6:
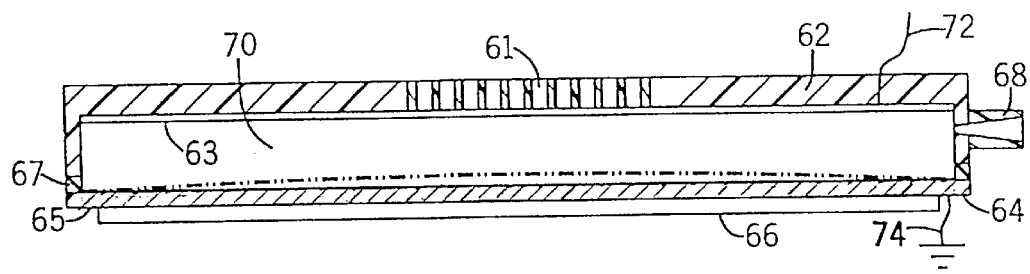

FIG. 2b NORMAL CONDITION

FIG. 2c DIRECTION OF RADIAL DECREASE
DIRECTION OF BENDING

DEVICE AND METHOD FOR DETECTING AND CONTROLLING LIQUID SUPPLY TO AN APPARATUS DISCHARGING LIQUIDS

BACKGROUND OF THE INVENTION

The present invention relates to an improved apparatus, such as a nebulizer apparatus, for discharging liquid, Nebulizem, or atomizers, are devices that generate a fine spray or aerosol, usually of liquid. A particularly useful application for nebulizers is to provide a fine spray containing a dissolved or a suspended particulate or colloidal phamaceutical agent for administration to a subject by inhalation. Such inhalation treatment is highly effective for conditions affecting the subject's respiratory organs. Further, since the lungs are close to the heart and the blood circulatory system of the body, drug administration by inhalation provides an effective and rapid delivery system to all organs of the body. Other applications include dispensing insecticides, paint, deodorants, water for humidification, etc. Other apparatuses which may incorporate the present invention include printers in which ink is discharged onto paper.

When dispensing a pharmaceutical agent, in many cases, a nebulizer is placed directly in the mouth or nose of the subject so that the spray can be entrained in the respiratory gases inhaled during normal, spontaneous breathing of the subject. In other cases, the subject breathes with the aid of a respiratory ventilator. A typical ventilator has a breathing circuit comprising an inhalation limb and an exhalation limb connected to two arms of an Y-connector. The third arm of the Y-connector is connected, via a patient limb, to a mouthpiece, mask or endotracheal tube for the subject. The ventilator provides a complete or partial supply of respiratory gases to the subject through the inhalation limb during inhalation. The contraction of the subject's lungs discharges gas through the exhalation limb during exhalation. When a nebulizer is employed in conjunction with a ventilator, it is typically placed in the patient limb but can also be placed in the inhalation limb.

Nebulizers currently in use for ventilator applications generate the spray either pneumatically or by means of ultrasonic vibrations. Pneumatic nebulizers are typically used with a liquid, such as an aqueous drug solution. High pressure driving gas is conducted through a nozzle to draw the drug from a drug supply for the nebulizer. The drug is discharged against a baffle or other means in a gas space of the nebulizer, breaking the liquid into a fine spray. The gas space is in fluid communication with the inhaled gas pathway of the breathing circuit so that the gas flow expelled from the nozzle along with the nebulized drug is conducted to the breathing circuit and ultimately to the subject.

Disadvantages in the use of pneumatic nebulizers include the following. If the nebulizer adds a significant quantity of gas, for example, up to five liters/minute, into the breathing circuit, the breathing gas composition may be affected. Due to passage of the driving gas through the nozzle, impingement of the drug on the baffle, etc., pneumatic nebulizers are noisy. Also, controlling the commencing and stopping of a drug agent spray is difficult and not very accurate, resulting in wastage of the drug.

The foregoing shortcomings of pneumatic nebulizer have led to the use of ultrasonic nebulizers employing a vibrating element, such as a piezoelectric crystal. Breathing gas composition and the on-off operation are easier to control with such nebulizers than in a pneumatic nebulizer. However, ultrasonic devices may require a large, bulky electrical power supply to power the ultrasonic vibrator and may not be able to nebulize colloidal or particulate suspensions.

In one type of ultrasonic nebulizer, the fine spray is produced dropping the liquid on, or otherwise applying it to, the vibrating element. See U.S. Pat. No. 5,443,059. U.S. Pat. No. 3,812,854 describes another type of nebulizer, for use in inhalation therapy, in which the spray is generated on the front surface of a vibrating, porous body. The pores of the body form a network of passages that enable the liquid to flow through the body. The liquid to be nebulized is supplied under pressure to the pores on the rear surface of the body, and forced through the pores to the front surface of the porous body where it is discharged as a spray. U.S. Pat. No. 5,487,378 describes a nebulizer in which the aerosol is formed using a mesh plate instead of a porous solid body. The mesh plate has a plurality of orifices for the liquid. The liquid or the nozzle assembly is vibrated ultrasonically by a piezoelectric element to nebulize a dose of liquid as it passes through the mesh plate. The supply of each dose through the nebulizer is sensed by a dose gauge.

A specific difficulty with nebulizers in which the liquid or the orifice assembly is vibrated ultrasonically, as by a piezoelectric element, to nebulize the liquid is control of the supply of liquid to the nebulizer so that the right amount necessary for proper operation is present in the nebulizer.

U.S. Pat. Nos. 5, 518,179 and 5,299,739 describe nebulizers in which capillary feed is used to supply liquid to the vibrating element. A further alternative for liquid supply is achieved by condensing a liquid vapor on one face of the membrane, the liquid thus condensed being dispensed in droplet form. See U.S. Pat. No. 5,518,179.

U.S. Pat. No. 5,938,117 describes an apparatus for dispensing liquids as an atomized spray and having a fluid supply system that transports fluid to an apertured oscillating surface. The fluid supply system is connected to an electronic flow control valve. The valve is connected to an electronic circuit. In the event of excessive delivery of liquid, the oscillation amplitude decreases and the current draw by the piezoelectric element decreases. A current sensor senses the reduced current draw and transmits an overflow signal to the flow control valve to reduce the delivery rate of liquid to the surface until the amount of fluid returns to a normal level.

BRIEF SUMMARY OF THE INVENTION

An object of the present invention is to provide an improved device and method for accurately controlling the supply of liquid in an apparatus discharging liquid. One such apparatus can comprise a nebulizer in which the accurate liquid supply enables the liquid to efficiently transformed into an aerosol. The invention may be employed with other types of apparatuses, such as those discharging ink for printing purposes.

The invention is particularly suited for use with a nebulizer employing an ultrasonically vibrating element but can also be extended to other type of nebulizers in which proper functioning and efficiency are dependent on control of the liquid into the nebulizer.

The above objects are obtained by an improved device and method for measuring the amount of liquid to be discharged that is present in the apparatus discharging the liquid. To this end, in a typical embodiment of the invention, a nebulizer includes a first member having holes through which the liquid passes to be nebulized. A second member is spaced from the first member so that a volume is defined in the nebulizer by the area of mutual overlap of the first and second members and the amount of spacing between them in the area of overlap. The first and second members have electrically conductive properties, as by being formed of conductive material or having an electrically conductive coating. The first and second members are electrically isolated from each other. The liquid to be nebulized is provided into the volume between the first and second members and circuitry is coupled to the first and second members to measure the capacitance between the members. The capacitance between the members indicates the amount of liquid in the volume defined in the nebulizer. A vibrator, such as a piezoelectric element, vibrates the liquid, as by bowing one of the first and second members, to carry out the nebulization of the liquid. The capacitance measuring circuit may be coupled to a liquid supply to cause the latter to, preferably intermittently, provide additional liquid to the volume as the nebulization of the liquid proceeds.

Various other features, objects, and advantages of the invention will be made apparent from the following detailed description and the drawings.

BRIEF DESCRIPTION OF THE SEVERAL VIEWS OF THE DRAWING

The foregoing objects and advantages, as well as the invention itself, will be more fully understood from the attached drawing and following detailed description.

In the drawings:

FIG. 1 is a general cross sectioned view of a nebulizer apparatus in which the present invention may be used, the operational environment for the nebulizer apparatus being shown in a generalized schematic form;

FIG. 2*a* is an exploded, partial, cross sectional view showing the apparatus of FIG. 1;

FIGS. 2*b* and 2*c* are schematic views showing the operation of the apparatus of FIG. 1;

FIG. 3 is a detailed view of certain elements used for detecting liquid supply by capacitive measurement;

FIG. 4 is a three dimensional portrayal representing the behavior of capacitance in the capacitive measurement employed in the present invention;

FIG. 5 is a schematic diagram of electrical circuitry for measuring capacitance;

FIG. 6 is a schematic view representing an alternative construction for the present invention; and FIG. 7 is a schematic view representing another alternative construction of the present invention.

DETAILED DESCRIPTION OF THE INVENTION

Apparatus 1, such as a nebulizer apparatus, incorporating the present invention is typically used in conjunction with breathing circuit 2, ventilator 3 and control unit 4, as shown in FIG. 1. The nebulizer 1 atomizes liquid solutions or suspensions for delivery to a subject, as for example as a drug treatment for a patient. Breathing circuit 2 includes inhalation limb 5, which is coupled to ventilator 3 at inhalation limb connector 6. Exhalation limb 7 is connected to ventilator 3 at exhalation limb connector 8. Inhalation limb 5 and exhalation limb 7 are connected to two arms of Y-connector 9. A third arm of Y-connector 9 is connected to one end of patient limb 10. The other end of patient limb 10 is directed to a mouthpiece, facemask, or endotracheal tube for the subject.

Ventilator 3 provides all or a portion of the respiratory gases for the subject by providing inhalation gases in inhalation limb 5. The inhalation gases pass through Y-connector 9 and into patient limb 10 for supply to the subject. On exhalation, the respiratory gases pass through patient limb 10, Y-connector 9, and exhalation limb 7 back to ventilator 3.

As shown in FIG. 1, the nebulizer apparatus 1 is preferably positioned in patient breathing circuit 2 as near the patient as possible to minimize the aerosol transport path, and to minimize the deposition of the aerosol on the breathing circuit walls. To this end, nebulizer apparatus 1 may be inserted in the breathing circuit between Y-connector 9 and patient limb 10. The Y-connector 9 has a socket 11 for receiving tubular projection 12 of adapter 13 for nebulizer apparatus 1. The tubular socket 14 of the adapter 13 receives the patient limb 10. The nebulizer apparatus is placed in opening 15 in adapter 13 and held in place with O-ring seal 16. When nebulizer apparatus 1 is not needed, or when the nebulizer apparatus is removed for cleaning or maintenance, a cap (not shown) may be fitted into or over the opening 15 to allow breathing circuit 2 to function in a normal manner. Alternatively, the entire adapter 13 containing nebulizer apparatus 1 may be removed from the breathing circuit and patient limb 10 reconnected to Y-connector 9. Control unit 4 for the nebulizer apparatus may be located at a distance from nebulizer apparatus 1 and may be incorporated in ventilator 3, if desired.

Nebulizer apparatus 1 is connected to a source of material to be nebulized. In the embodiment shown in FIG. 1, conduit 17 and transport line 17*a* supply material from reservoir 18 to apparatus 1. Reservoir 18 can be placed at a desired location and can be proximate to, or remote from, nebulizer apparatus 1. A control valve 19 is provided between the supply conduit 17 and the transport line 17*a*. Electrical control signals are supplied to control valve 19 via cable 20 from control unit 4. The material to be nebulized is usually a liquid and can comprise a solution, or a particulate or colloidal suspension, of a pharmaceutical agent. For purposes of explanation, the material undergoing nebulization is hereinafter generally described as a liquid. Reservoir 18 is pressurized by pump in control unit 4. In the embodiment shown in FIG. 1, a pump inside control unit 4 supplies a pressurizing gas to reservoir 18 through pressure line 21.

Nebulizer apparatus 1 is shown in detail in FIGS. 2*a*, 2*b*, 2*c*. Nebulizer apparatus 1 shown in the cross sectional, exploded view of FIG. 2*a* has annular housing 22, which mounts the apparatus in adapter 13. Housing 22 is formed of plastic or similar material. Lip 23 is formed on the lower edge of housing 22 and contains O-ring 24. Housing 22 is attached to plug member 32 by rotatable fastening means formed by openings 40 and 41 and associated projections 42 and 43. Projections 42 and 43 extend from the sides of plug member 32 and fit into openings 40 and 41 formed in the housing 22. Plug member 32 may be retained or removed from housing 22 by tuning and pulling or turning and pushing the plug member with respect to housing 22. This allows the portions of apparatus 1 carrying out the nebulizing of the liquid and positioned in cavity 33, to be removed at the end of therapy, for replacement, or for cleaning when a different drug is to be administered to the subject.

O-ring 24 seals the disc-like plate 25 to lip 23. Plate 25 is shown with enlarged thickness in FIG. 2*a* and may be formed of a conductive material such as brass. Plate 25 contains a central opening 26. Mesh plate 27 is mounted across central opening 26 of plate 25 by gluing with conducting glue, brazing, welding, or other suitable technique.

Mesh plate 27 is a relatively thin plate having a plurality of holes 28. Mesh plate 27 may be about 0.02 mm thick. The diameter of the holes at front surface 44 is preferably approximately 2–15 $\mu$m. Such holes may be formed in the plate by an electroforming process, which process produces holes of increasing diameter toward rear surface 45 of mesh plate 27. However, straight holes will work equally well, the primary criterion being that the exit diameter in front surface 44 of mesh plate 27 is such as to form droplets of the desired size.

Front surface 44 of mesh plate 27 is exposed to the pressure of the breathing gases in breathing circuit 2. These pressures will vary during inhalation and exhalation conditions in the breathing circuit. For example, with artificial ventilation, breathing circuit pressures may increase up to 100 mbar during inspiration and thereafter decrease during expiration. Disc-like plate 25 is provided with pressure balancing channel 37, as shown in FIG. 2*a,* that connects the volume between plug member 32 and plate 25 with breathing circuit 2 for equalizing the prevailing pressure at both sides of mesh plate 27. The pressure balancing provided by channel 37 prevents breathing gas from flowing through the holes in mesh plate 27, in opposition to the liquid being nebulized, which might otherwise degrade the operation of nebulizer apparatus 1 and avoids pressure stressing of mesh plate 27 and causing leaks to occur through the mesh plate.

In the nebulizer apparatus shown in FIGS. 2*a,* 2*b,* and 2*c,* a vibrating element, such as a piezoelectric element 29, is mounted adjacent the surface of plate 25 which is the upper surface of the plate when the nebulizer is oriented as shown in FIG. 2*a*. Specifically, piezoelectric element 29 is spaced from plate 25 by a small gap 30 and secured to plate 25 about its periphery by a conductive glue, brazing, welding, or other suitable technique, shown as 31 in FIGS. 2*a,* 2*b,* and 2*c*. Piezoelectric element 29 has a central opening corresponding to the central opening 26 of plate 25.

Plug member 32 is formed from a non-conductive material, such as plastic. Plug member 32 has a lower lip 34 containing an O-ring 35. Plug member 32 is placed on top of plate 25 so that the plate is between O-rings 24 and 35 when the plug member is placed in cavity 33 defined by housing 22.

An electric power terminal 38 extends through plug member 32. The lower end of terminal 38, which terminal may be in the form of a spring-loaded pin, contacts piezoelectric element 29. The upper end of terminal 38 is connected to cable 20 shown in FIG. 1. A second electrical power terminal 39 also extends through plug member 32. The lower end of terminal 39 contacts conductive plate 25. The upper end of terminal 39 is also connected to cable 20. Terminal 38, and terminal 39 which may be electrically grounded, apply a voltage to piezoelectric element 29. Grounded terminal 39 may also be used for capacitive measurement in conjunction with a plate 36 at the end of liquid transport line 17*a* which also functions as an electrical terminal and is hereinafter described in detail.

A central liquid transport line 17*a* extends through plug member 32 so that the plate 36 at the end of liquid transport line 17*a* is proximate to the upper surface of plate 25 and mesh plate 27. Plate 36 is formed of an electrically conductive material, but it is electrically isolated from its surroundings and from mesh plate 27 to allow its use in capacitance measurement of the presence of liquid in nebulizer apparatus 1.

In operation, valve 19 is opened in response to a signal from cable 20 and liquid flows through conduit 17 and transport line 17*a* due to the pressurizing gas in reservoir 18. The liquid flows out the end of transport line 17*a* as shown in FIG. 2*a,* into the volume between the plate 36 and the upper surface 45 of mesh plate 27. The cohesive forces in the liquid create a column of liquid between the plate 36 and mesh plate 27, as shown in FIG. 3.

To control the transport of liquid from reservoir 18 into the nebulizing apparatus 1, plate 36 and mesh plate 27 function as sensing electrodes that detect the presence and amount of the liquid supply between the plate 36 and the upper or rear surface 45 of mesh plate 27 by alteration of the capacitance between the two electrodes. FIG. 3 shows a more detailed picture of the capacitance electrodes and the behavior of the liquid between them. In FIG. 3 $R_f$ is a radius of liquid column 50 between plate 36 and mesh plate 27, $R_p$ is a radius of plate 36 and L is a distance between the two plates.

The capacitance existing between the plate 36 and mesh plate 27 is dependent on the different variables present, as follows:

$$C = \frac{\varepsilon_0 \cdot \pi \cdot [\varepsilon_{air} \cdot R_p^2 - \varepsilon_{air} \cdot R_f^2 + \varepsilon_{liquid} \cdot R_f^2]}{L}$$

where $\in_O$=dielectric coefficient of a vacuum $\in_{air}$=dielectric coefficient of the air between the two plates 27, 36

$\in_{liquid}$=dielectric coefficient of the liquid between the two plates $R_p$=radius of the plate 36

$R_f$=radius of the liquid column 50 between the two plates 27, 36

L=distance between the two plates 27, 36.

The dielectric coefficient of the liquid to be nebulized is much higher than the dielectric coefficient of the air and enables the amount of liquid or the radius of the liquid column to be measured accurately between the two plates.

In order for the capacitive measurement to function properly, the distance between plate 36 and mesh plate 27 has to be adjusted to a suitable distance. If the distance between the two plates is too great, the capacitance values between the plates becomes too low to obtain an accurate measurement result. If the distance between the plates is too little, the operation of the nebulizer apparatus may be adversely affected, as noted below.

Reliable results can be obtained when capacitance values vary over a range of a few $p_F$ and this will be obtained with radius $R_p$ of 2.5 mm for plate 36 and a distance L of 0.5 mm between the plate 36 and mesh plate 27.

The area of the plate 36 also has an effect on sensitivity of the capacitive measurement. Shape of the area of plate 36 can have different forms. While a rounded or a square shape for plate 36 is easier to analyze, other forms such as triangular, rectangular, star, or other multi-sided configurations may be used. A round plate is discussed below for explanatory purposes. If the radius of the plate 36 is increased, the overlap area of the electrodes becomes larger and higher values of capacitance will be achieved. The radius of the plate 36 can also be made smaller, but the distance between the plate 36 and mesh plate 27 must be decreased at the same time to maintain a certain level of capacitance.

FIG. 4 shows the dependence of capacitance in pico farads on the z-axis with respect to the radius $R_f$ of liquid column in micrometers on the x-axis and the distance L between the plates 27 and 36 in micrometers on the y-axis. It can be seen that both increasing the radius of liquid column $R_p$, in other words increasing the overlapping area of plates 27 and 36 where the liquid column may exist and decreasing the distance L between the plates 27 and 36 increase the measured values of capacitance fairly exponentially.

With a continued supply of liquid, the liquid column 50 between the plate 36 and the rear surface 45 of mesh plate 27 will grow in the radial direction and significantly increase the capacitance measured between the two plates. The capacitance between the two sensing electrodes is inputted to sensor circuitry inside the nebulizer 1 or inside the control unit 4 via cable 20 and is used by the control unit 4 to close the valve 19 in the liquid supply conduit 17.

When the capacitance decreases due to the liquid receding away between plate 36 and mesh plate 27 during operation of nebulizer apparatus 1, the control valve 19 is opened to allow flow of liquid from the end of transport line 17*a*. The delivery of nebulized liquid can be carried out responsive to the activation of the vibration of mesh plate 27 by intermittently supplying liquid when the amount of liquid between the mesh plate 27 and the plate 36 is reduced.

FIG. 5 shows an example of a circuit 100 to measure capacitance between plates 27 and 36 serving as the sensing electrodes. In this circuit, element 102 may comprise a capacitively controlled RC-oscillator, the output of which is a continuous train of pulses. Change in capacitance between elements 27 and 36, as reflected in the signal in conductor 104, changes the frequency or pulse width of the output. The continuous pulse train may be low pass filtered by a filter (not shown) to provide a DC-signal at output 108 having a linear response with respect to measured capacitance. When the capacitive measurement is carried out during the vibrating of mesh plate 27, these vibrations cause the capacitance between elements 27 and 36 to alter in phase with the vibration. The result is a modulation of the capacitance related output signal by a varying signal. Additional filtering may be employed to filter out the varying signal produced by the vibrations of mesh plate 27.

In operation, alternating voltage is supplied from a power source inside the control unit 4 though cable 20 and terminals 38 and 39 to piezoelectric element 29, which vibrates the element. The alternating voltage causes the element 29 to contract from the normal condition, shown in FIG. 2*b,* to a radially decreased condition shown in FIG. 2*c* and then return to the normal condition. Due to the joinder of piezoelectric element 29 to plate 25 about the periphery of the element, the radial size reduction of piezoelectric element 29 causes plate 25 to bow, as shown in FIG. 2*c,* and then return to the flat condition, shown in FIG. 2*b,* when piezoelectric element 29 returns to the normal state. The action of plate 25, as shown in FIGS. 2*b* and 2*c* moves liquid fed to the upper surface 45 of mesh plate 27 through holes 28 onto the front surface 44 of mesh plate 27 by inertia and the motion of the liquid in phase difference compared to the vibration of mesh plate 27. At the front surface 44 of the vibrating mesh plate 27, the atomized liquid will grow into drops at each hole 28 due to the liquid surface tension. The drops will increase in size until the expelling forces arising from the movement of mesh plate 27 and the mass of each drop exceeds the holding force determined by the size of the holes 28 in mesh plate 27 and the surface tension of the liquid at which point the drop is expelled. The drops expelled from mesh plate 27 pass through the housing 22 into the patient limb 10, and to the subject during inhalation. As noted above, the action of plate 25, as shown in FIGS. 2*b* and 2*c* also has an effect on capacitive measurement due to the variation of distance L between the plate 36 and mesh plate 27, but this interference, having a frequency of mesh plate vibration, can be filtered from the output signal of the circuitry shown in FIG. 5.

The sensitivity of capacitive measurement becomes better as the distance L between the two plates becomes smaller, as can be seen from FIG. 4. However the distance L between plates 27 and 36 should not be too small. If the distance between the plates becomes too small, the amount of liquid is greatly reduced and the compressing force directed to the liquid caused by the bowing action of vibrating plate 25 with respect to plate 36 is increased. This compressing force directed to the liquid will squeeze the liquid under the pressure through the holes 28 in mesh plate 27. This squeezing action differs from the desired action where the discharging of liquid through the holes of the mesh plate is caused by the inertia and the motion of the liquid in phase difference compared to vibrating mesh plate. At some frequencies this squeezing action may work equally well as the desired action, but at frequencies where the desired action occurs it may damp the vibrations of plate 25 and interfere with the functioning of mesh plate 27 preventing the droplets from being formed.

FIG. 6 shows an example of another type of nebulizer apparatus construction having capacitive measurement to control the supply of liquid for the atomizing means. In this construction cover 62, which may be of plastic or silicone, and bottom part 64, which is a bimorph, are closed tightly together with an elastic joint 67 to form a chamber 70 for the liquid to be nebulized. A nozzle assembly 61, such as a mesh plate, is glued into a hole in the middle of the surface of cover 62 or, alternatively, a nozzle or nozzles can be integrated directly into cover 62, as shown in FIG. 6. The lower surface of cover 62, when the nebulizer apparatus is oriented as shown in FIG. 6, has an electrically conductive coating 63, which functions as a sensing electrode for capacitive measurement, via conductor 72. The bottom part 64, which is a bimorph, is composed of piezoelectric crystal 66 attached to metal plate 65. Metal plate 65, which is the upper surface of bottom part 64, functions as a counterpart for the sensing electrode 63. To ensure that the capacitive measurement functions properly, sensing electrode 63 and the upper surface of bottom part 64 must be electrically isolated from each other. This can be achieved by providing an electrically isolating coating on both or at least on one of these electrically conductive surfaces. Vibrating element 66, such as a piezoelectric crystal, which is operated in the radial mode, shown in FIGS. 2*b* and 2*c,* is mounted on the lower surface of metal plate 65 by electrically conductive glue or other suitable technique. This enables the metal plate 65 to also function as an electrical ground for the vibrating element 66 via conductor 74. Tube 68 extends through the side wall of cover 62 so that the chamber 70 can be filled with liquid. Tube 68 is tapered toward the chamber and functions as a diffuser, preventing reverse flow of the liquid.

In operation, an alternating voltage supplied to vibrating element 66 forces the bottom pat 64 to vibrate between two states. In one state, vibrating element 66 causes bottom part 64 to bend, as shown with a dotted line in the FIG. 6. The other state is the normal flat state. The inward bending of bottom part 64 decreases the volume of chamber 70 and increases the pressure on the liquid inside it. The increase in pressure, when applied to the liquid inside the chamber forces the liquid through the nozzle or nozzles 61 placed in the cover 62. As the aerosol is generated, air may flow through the nozzle or nozzles into the chamber 70 due the under pressure formed when the bottom part 64 returns to the normal state. The air inside the chamber will hamper the generation of aerosol because the pressure generated during the bent state of bottom part 64 has an effect mostly on the air due to its higher compressibility as compared to liquid. The amount of air flowing into chamber 70 and the emptying of chamber 70 of liquid can be measured with the capacitive measurement between coating 63 and metal plate 65 and more liquid can be fed to chamber 70 through tube 68 to keep the chamber filled.

Figure 7:
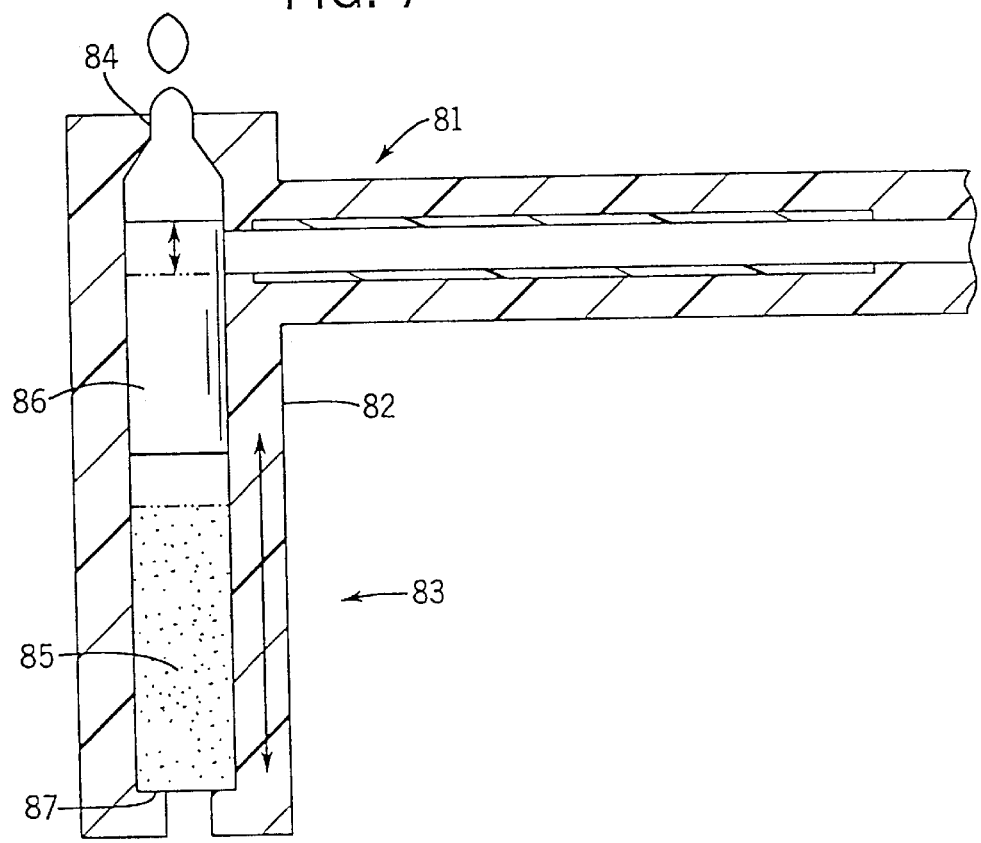

FIG. 7 shows a further embodiment of the improved device for measuring the amount of liquid to be discharged by an apparatus. In contrast to the embodiments previously described, the measuring device of FIG. 7 is located in the transport line that supplies the liquid to be discharged from a reservoir to the apparatus rather than in a cavity within the apparatus. Specifically, and as shown in FIG. 7, liquid to be discharged is supplied in transport line 81 to housing 82 of discharge apparatus 83. Discharge apparatus 83 includes one or more nozzles 84 in the housing. Housing 82 contains piezoelectric element 85 attached to piston 86 and to the bottom wall 87 of housing 82. When piezoelectric element 85 is energized by high frequency alternating current, piston 86 alternately moves between the position shown by the dashed line in FIG. 7 and the position shown by the solid line. When piston 86 is in the position shown by the dashed line, liquid from transport line 81 enters housing 82. When piston 86 moves to the position shown in the solid line, liquid in housing 82 is discharged through nozzle 84.

To control the supply of liquid to housing 82 of discharge apparatus 83, two opposite walls 87 and 88 of transport line 81 are provided with electrically conductive members 89 and 90, respectively. Members 89 and 90 function as sensing electrodes for capacitive measurement of the presence and amount of liquid in transport line 81 in the same manner as described above. The measurement carried out by members 89 and 90 can be used to control the provision of liquid to transport line 81 to ensure that the transport line is full of liquid.

The above described technique of capacitive measurement is particularly suitable for micro mechanical apparatuses using elements formed of silicon.

It is recognized that other equivalents, alternatives, and modifications aside from those expressly stated, are possible and within the scope of the appended claims.

What is claimed is:

1. In an apparatus for discharging liquid, an improved device for measuring the amount of liquid that is present in the apparatus, said improved device comprising:

a first member having at least one hole through which the liquid passes to be discharged from the apparatus along a direction of discharge;

a second member spaced behind said first member along the direction of liquid discharge;

means for providing liquid between said first and second members;

said spaced first and second members establishing a volume in the apparatus between the members for receiving the provided liquid, the volume being defined in the apparatus by an area of mutual overlap of said first and second members and the amount of spacing between said first and second members in the area of overlap, said first and second members being formed to constrain the provided quantity of liquid between the members so that a dimension of the liquid quantity between the first and second members that is normal to the direction of the spacing between said first and second members is dependent on the amount of liquid in the volume, said first and second members being formed to establish a mutual capacitance that reflects the amount of liquid that is present in the volume; and a capacitance measuring unit coupled to said first and second members to determine the amount of liquid in the apparatus.

2. The improved device according to claim 1 wherein said first and second members have electrically conductive properties, said first and second members being electrically isolated from each other.

3. The improved device according to claim 1 wherein said first member is a plate having a plurality of holes.

4. The improved device according to claim 2 wherein at least one of said first and second member is formed of conductive material.

5. The improved device according to claim 3 wherein said plate is formed of conductive material.

6. The improved device according to claim 2 wherein at least one of said first and second member has an electrically conductive coating.

7. The improved device according to claim 1 wherein said liquid providing means is coupled to said second member for providing liquid through said second member into the volume.

8. The improved device according to claim 1 wherein at least one of said first and second member is round.

9. The improved device according to claim 1 further including a vibrator coupled to one of said first and second members, said vibrator being energizable to vibrate the member to which it is coupled.

10. The improved device according to claim 9 wherein said vibrator is a piezoelectric vibrator.

11. The improved device according to claim 10 wherein said vibrator creates vibrations in the liquid by bowing one of said first and second members.

12. The improved device according to claim 1 wherein said capacitance measuring unit is coupled to said liquid providing means for causing said liquid providing means to provide liquid into the volume responsive to the determination of the amount of liquid in the apparatus.

13. The improved device according to claim 12 wherein said liquid providing means is further defined as intermittently providing liquid into the volume between the first and second members.

14. The improved device according to claim 1 wherein said capacitance measuring unit comprises a capacitively controlled RC-oscillator receiving an input from at least one of said first and second members and providing a pulse train output, and filter means for filtering said pulse train output to provide a signal indicative of the capacitance existing between said first and second members.

15. The improved device according to claim 14 wherein said capacitance measuring unit is coupled to said liquid providing means for controlling the provision of liquid into the volume.

16. The improved device according to claim 1, 2, 3, 7, 9, 10, or 12 further defined as an improved device for measuring the amount of liquid that is present in a nebulizer apparatus.

17. In an apparatus for discharging liquid, an improved device for measuring the amount of liquid that is present in a liquid transport line for the apparatus, said improved device comprising:

a first member in the transport line and a second member in the transport line spaced from said first member so that a volume is defined in the transport line by an area of mutual overlap of said first and second members and the amount of spacing between said first and second members in the area of overlap, said first and second members being formed to constrain the provided quantity of liquid between the members so that a dimension of the liquid quantity between the first and second members that is normal to the direction of the spacing between said first and second members is dependent on the amount of liquid in the volume, said first and second members being formed to establish a mutual capacitance that reflects the amount of liquid that is present in the volume; and a capacitance measuring unit coupled to said first and second members to determine the amount of liquid that is present in the liquid transport line.

18. The improved device according to claim 17 wherein said first and second members have electrically conductive properties, said first and second members being electrically isolated from each other.

19. The improved device according to claim 18 wherein at least one of said first and second member is formed of conductive material.

20. The improved device according to claim 17 wherein said capacitance measuring unit is coupled to liquid providing means for causing the liquid providing means to provide liquid into the volume responsive to the determination of the amount of liquid in the apparatus.

21. The improved device according to claim 20 wherein said liquid providing means is further defined as intermittently providing liquid into the volume between the first and second members.

22. The improved device according to claim 17 or 18 further defined as an improved device for measuring the amount of liquid that is present in the liquid transport line for a nebulizer.

23. A nebulizer for nebulizing a liquid comprising:

a housing;

a chamber in said housing for receiving liquid to be nebulized;

a first member mounted to said housing and having holes through which the liquid passes when nebulized to be discharged from the nebulizer along a direction of discharge, said chamber being in fluid communication with said first member;

a second member mounted to said housing and spaced behind said first member along the direction of liquid discharge;

means for providing liquid between said first and second members;

said spaced first and second members establishing a volume in the chamber between the members for receiving the provided liquid, the volume being defined by an area of mutual overlap of said first and second members and the amount of spacing between said first and second members in the area of overlap, said first and second members being formed to constrain the provided quantity of liquid between the members so that a dimension of the liquid quantity between the first and second members that is normal to the direction of the spacing between said first and second members is dependent on the amount of liquid in the volume, said first and second members being formed to establish a mutual capacitance that reflects the amount of liquid that is present in the volume;

a vibrator for creating vibrations in the liquid for causing the liquid to pass through the holes in said first member; and a capacitance measuring unit coupled to said first and second members to determine the amount of liquid that is present in the nebulizer, said unit being coupled to said liquid providing means for controlling the provision of liquid into the volume in accordance with the capacitance measured by said capacitance measuring unit.

24. A nebulizer according to claim 23 wherein said first and second members have electrically conductive properties.

25. A nebulizer according to claim 23 wherein said first member is a thin plate having a plurality of holes.

26. A nebulizer according to claim 24 wherein at least one of said first and second members is formed of a conductive material.

27. A nebulizer according to claim 24 wherein at least one of said first and second members has an electrically conductive coating.

28. A nebulizer according to claim 24 wherein said liquid providing means is couple to said second member for providing liquid through said second member to the volume.

29. A nebulizer according to claim 23 wherein said liquid providing means intermittently provides liquid into the volume.

* * * * *